(12) United States Patent
Sabel et al.

(10) Patent No.: US 6,464,356 B1
(45) Date of Patent: Oct. 15, 2002

(54) PROCESS AND DEVICE FOR THE TRAINING OF HUMAN VISION

(75) Inventors: Bernhard A. Sabel; Erich Kasten, both of Magdeburg (DE)

(73) Assignee: Novavision AG, Magdeburg (DE)

( * ) Notice: Subject to any disclaimer, the term of this patent is extended or adjusted under 35 U.S.C. 154(b) by 0 days.

(21) Appl. No.: 09/784,450

(22) PCT Filed: Aug. 27, 1998

(86) PCT No.: PCT/EP98/05505

§ 371 (c)(1),
(2), (4) Date: Apr. 25, 2001

(87) PCT Pub. No.: WO00/12042

PCT Pub. Date: Mar. 9, 2000

(51) Int. Cl.$^7$ ................................................ A61B 3/00
(52) U.S. Cl. ...................................................... 351/203
(58) Field of Search ................................ 351/200, 201, 351/203, 222, 223, 224, 246, 46

(56) References Cited

U.S. PATENT DOCUMENTS

| 4,971,434 A | | 11/1990 | Ball | |
| 6,062,687 A | * | 5/2000 | Lofgren-Nisser | 351/46 |

FOREIGN PATENT DOCUMENTS

DE           93 05 147        9/1994

OTHER PUBLICATIONS

E. Kasten, et al., Restorative Neurology and Neuroscience, vol. 8, No. 3, pp. 113–127, "Visual Field Enlargement After Computer Training in Brain–Damaged Patients Whit Homonymous Deficits: An Open Pilot Trial", Aug. 1995.

K. K. Ball, et al., Journal of the Optical Society of America A, vol. 5, No. 12, pp. 2210–2219, "Age and Visual Search: Expanding the Useful Field of View", Dec. 1998.

E. Kasten, et al., Spatial Vision, vol. 10, No. 4, pp. 499–503, "Programs for Diagnosis and Therapy of Visual Field Deficits in Vision Rehabilitation", 1997.

J. Zihl, Zeitschrift fuer Neuropsychologie, No. 2, pp. 95–101, "Zur Behandlung Von Patienten Mit Homonymen Gesichtsfeldstoerungen", 1990.

* cited by examiner

*Primary Examiner*—George Manuel
(74) *Attorney, Agent, or Firm*—Oblon, Spivak, McClelland, Maier & Neustadt, P.C.

(57) ABSTRACT

The present invention concerns a process for training the visual system of a human by presenting optical stimuli to said human, said stimuli being presented to a zone within the intact visual field of said human and to a zone outside the intact visual field of said human, the latter zone comprising a zone to be trained, thereby allowing an improvement of the vision in said latter zone, said process comprising the steps of locating and defining a zone of deteriorated vision or residual visual function or partial visual system injury ("transition zone") within the human's visual system; defining a training area which is located within said transition zone; training the human's visual system by presenting visual stimuli to the human's visual system, the majority of said visual stimuli being presented in or near said transition zone; recording changes in the characteristics of the human's visual system; adapting the location and definition of the stimulus presentation to said transition zone according to said changes; and reiterating the previous steps continuously so as to extend the human's intact visual field into said transition zone and said transition zone into a zone of more deteriorated vision or a zone of less residual visual function or a zone of substantially complete visual system injury, and a device for conducting said process.

21 Claims, 4 Drawing Sheets

PROCESS AND DEVICE FOR THE TRAINING OF HUMAN VISION

The present invention concerns a process and device for the training of human vision. In particular, the invention relates to a process and apparatus by which a change of the visual performance of persons in need of a training for improvement or completion of their vision can be affected by stimulating their visual system with optical stimuli.

Impairments of a human's visual system may either result from an incomplete or impaired development of the visual system during infancy or from a deterioration either continuously and naturally due to ageing of the person or more or less abruptly due to diseases or accidents more or less severely influencing the visual system. It was, for example, found that the vision of children can substantially be improved by regular sessions of training their visual system, e. g. in cases of squinting. On the other hand, persons whose vision was deteriorated for any reason may either stop the deteriorating development or even improve their vision by a specific training adapted to the cause of deterioration of their visual system. The present invention intends to provide a process and device for training and improving a human's vision in all conceivable cases of impairment where the presentation of optical stimuli to the visual system of a person having need for an improvement of the vision may promise a successful removal of the cause of impairment and/or increase his/her performance.

In recent years computer-technology has been utilized to train mental functions of the human brain. For example, the prior art reports on methods to treat temporal processing deficits of language-learning impaired children using computer-training as a paradigm (M. M. Merzenich et al., Temporal processing deficits of language-learning impaired children ameliorated by training; Science 271, 77–81 (1996)). It is not clear, however, whether computer-based training can facilitate other sensory modalities such as visual functions after damage to the brain.

Brain injury, which may result from stroke or trauma, often impairs visual functions. Patients typically loose sight in one half of the visual field while the other side often remains unimpaired. This partial blindness is generally considered untreatable because it is the long-held belief that proper vision requires a highly specific neuronal organization (D. H. Hubel, T. N. Wiesel, Receptive fields, binocular interaction and functional architecture in the cat's visual cortex, J. Physiol. 106–154 (1962)). Despite this specificity in neuronal organization, there is, however, a considerable degree of plasticity in the injured visual system (U. Eysel, O. J. Gruesser, Increased transneuronal excitation of the lateral geniculate nucleus after acute differentiation, Brain Res. 158, 107–128 (1978); J. H. Kaas et al., Reorganization of retinotopic cortical maps in adult mammals after lesions of the retina, Science 248, 229–231(1990); C. D. Gilbert, T. N. Wiesel, Receptive field dynamics changes in adult cerebral cortex, Nature 356,150–152 (1992)). Lost visual functions can recover spontaneously to some extent in animals (J. Sautter, B. A. Sabel, Recovery of vision despite progressive loss of retrogradely labelled retinal ganglion cells after optic nerve crush, Europ. J. Neurosci. 5,680–690 (1993); B. A. Sabel, E. Kasten, M. R. Kreutz, Recovery of vision after partial visual system injury as a model of post-lesion neuroplasticity, Adv. Neurol. 73, 251–276 (1997); T. N. Wiesel, D. H. Hubel, Extent of recovery from the effects of visual deprivation in kittens, J. Neurophysiol. 28, 1060–1072 (1965); K. L. Chow, D. L. Steward, Reversal of structural and functional effects of long-term visual deprivation in cats, Exp. Neurol. 34, 409–433 (1972)) and man (H. - L. L. Teuber, W. S. Battersby, M. B. Bender, Visual field defects after penetrating missile wounds of the brain, Cambridge, Mass., Harvard University Press (1960)). At least some of this spontaneous post-lesion neuroplasticity of the adult visual system is due to extensive receptive field reorganization following lesions in retina or cortex (U. Eysel, O. Gruesser, loc. cit.; J. H. Kaas et al.. loc. cit.).

In the prior art, training methods have been disclosed that can be used to improve visual functions of brain damaged monkeys (A. Cowey, Perimetric study of field defects in monkeys after cortical and retinal ablations, Quart. J. Exp. Psychol. 19, 232–245 (1967)) and of men (J. Zihl, Zur Behandlung von Patienten mit homonymen Gesichtsfeldstörungen, Z. Neuropsychol. 2, 95–101 (1990); E. Kasten, B. A. Sabel, Visual field enlargement after computer training in brain damaged patients with homonymous deficits: an open pilot trial, Restor. Neurol. Neurosci. 8, 113–127 (1995)). However, in humans it has not generally been accepted that training can improve vision. Nevertheless, several observations were made that suggest that humans with visual system damage may benefit from visual training.

The first observation that visual training may be effective in humans is the study by Zihl et al. (loc. cit.), who found that repeated presentation of visual stimuli and measurements of incremental thresholds in the same retinal location results in small expansions of visual field borders in persons with visual field defects. Repeated testing in this situation requires, however, an experimenter to carry out the training with the person to be trained, i.e. this method cannot be used by the person independently. Thus, it is extremely time consuming for both the person and the experimenter.

To overcome this manual approach of presenting visual stimuli, several devices have been disclosed in the prior art with which automated testing can be achieved. Although their efficacy has only been shown in a few individual persons and a strictly planned clinical trial was never carried out, there have been claims that these methods may improve visual functions. However, because these prior art devices have been too complicated to use and inefficient in their application, they have not been widely accepted in clinical practice.

In the document No. DE-U 93 05 147 issued to Schmielau, for example, a device for training the visual system of humans is described consisting of a large size hemispheric half bowl. Here, arrays of small light bulbs are positioned in a large diameter semicircle. Light stimuli are presented by illuminating sequences of said light bulbs arranged closely to each other such that they may stimulate the visual field in different excentricities from the center which has to be visually fixed. While this device does allow assessment and training of the entire visual field in its full extent, it has several disadvantages which preclude its widespread use. The disadvantages are (1) its size, (2) the inflexible position with which visual stimuli can be presented, and (3) the absence of any teaching of orienting the training according to the residual visual functions. Due to the lack of presentation strategy, the use of the Schmielau prior art device requires extended time periods. In addition, the half bowl used for training is inpracticable for home use.

The limitation of the Schmielau invention is apparent from the FIG. 4 of said document: There, as also described in the classical text books, the visual system of a human is shown by areas which are either intact or deficient. There is no mention of areas of impaired, residual visual functions based on which a visual field training may be performed.

One may presume that computers might be useful to replace such a large size, unpracticable device, but Schmielau (loc. cit.) states that this is not possible.

Therefore, since it is clearly stated that computer controlled training is not useful for purposes of visual field training, the use of computers was always refused in the prior art by those skilled in the art.

In contrast to the general expectations in the art, we have surprisingly found that a computer-controlled training procedure for visual functions of a human can contribute considerably to an improvement of the training effect. There was, therefore, developed a computer program which has been described elsewhere (E. Kasten, B. A. Sabel, Visual field enlargement after computer training in brain damaged patients with homonymous deficits: an open pilot trial. Restor. Neurol. Neurosci. 8, 13–127 (1995)). The principle advantage of using a computer-controlled device is that it is much smaller and that it allows the continuous recording of the person's performance. However, the programs described by Kasten et al. (loc. cit.) present the stimuli in random order on a computer screen, without considering the person's actual performance in the visual task. Therefore, training has been time consuming and inefficient, though this method has been shown effective in an early pilot study.

In the paper published by Kasten et al. (1997; loc. cit.) the program has been described. "Sehtra", for instance, presents small light stimuli of variable luminance in all parts of the visual field, but it does not adapt to the person's actual performance in the different field sectors. It is noted that the stimuli are presented at random by a predetermined sector of the monitor to the person's visual field, without considering the actual nature of the deficit and the zone of partial Visual system injury or residual visual function (so-called "transition zone").

Because of this, the persons to be trained have to respond to stimuli addressing areas of their visual field which are, in fact, intact. As a consequence, much time is spent by the person for purposes which are useless therapeutically. This situation produces an unnecessary demand on the person's time and patience. Boredom and loss of motivation has therefore often been observed.

In order to overcome this limitation, it was an object of the present invention to provide a process and device for the training of human vision, which avoid the known disadvantages of the prior art. In addition, it was an object of the invention to provide a process and device for the training of human vision which take into account the training of zones of the person's visual system where residual visual functions are maintained or where the natural vision is partly deteriorated only or where the natural vision is to be maintained on a high quality level (so-called "transition zones"). It was a further object of the invention to provide a process and device for the training of human vision which allow an extension of the person's visual field into said transition zone and of said transition zone into a zone of substantially complete visual system injury in the case that the vision of a person is severely injured. In addition, it was an object of the invention to provide a process and device for the training of a human's vision which may be handled not only in usual training centers under the supervision of an experienced experimenter but also in the person's private environment by himself.

Surprisingly, the above objects were achieved by the present invention. The inventors conceived a new manner by which visual stimuli are presented on a simple device for emitting optical stimuli to the visual system of a human.

In a very general sense, the invention relates to a process for training the visual system of a human by presenting optical stimuli to said human, said stimuli being presented to a zone within the intact visual field of said human and to a zone outside the intact visual field of said human, the latter zone comprising a zone to be trained, thereby allowing an improvement of the vision in said latter zone, said process comprising the steps of locating and defining a zone of deteriorated vision or residual visual function or partial visual system injury ("transition zone") within the human's visual system;

defining a training area which is located within said transition zone;

training the human visual system by presenting visual stimuli to the human visual system, the majority of said visual stimuli being presented in or near said transition zone;

recording changes in the characteristics of the human's visual system;

adapting the location and definition of the stimulus presentation to said transition zone according to said changes; and reiterating the previous steps continuously so as to extend the human's intact visual field into said transition zone and said transition zone into a zone of more deteriorated vision or a zone of less residual visual function or a zone of substantially complete visual system injury.

In a further embodiment, the invention relates to a device for training the visual system or vision of a human allowing the above training process to be conducted. The device essentially comprises a central data processing means for recording, storing, processing and emitting data from the other means of the apparatus;

at least one visual stimuli emitting means;

a fixation point means allowing the fixation of the person's view;

means for entering the person's response on visual stimuli perceived;

means for allowing a control of said at least one optical stimuli presenting means in accordance with the performance of the person responding on optical stimuli perceived.

In a preferred embodiment of the invention, said device enables the steps of locating and defining a zone of deteriorated vision or residual visual function or partial visual system injury ("transition zone") within the human's visual system;

defining a training area which is located within said transition zone;

training the human's visual system by presenting visual stimuli to the human's visual system, the majority of said visual stimuli being presented in or near said transition zone;

recording changes in the characteristics of the human's visual system;

adapting the location and definition of the stimulus presentation to said transition zone according to said changes; and reiterating the previous steps continuously so as to extend the human's intact visual field into said transition zone and said transition zone into a zone of more deteriorated vision or a zone of less residual visual function or a zone of substantially complete visual system injury.

Thus, the inherent feature of the present invention is that the training by stimulus presentation predominantly occurs in or near the zone of deteriorated vision or the zone of residual visual function or the zone of partial visual system injury, i. e. in the transition zone, which is the zone intended to be trained and a presentation of stimuli in the intact visual field is considerably reduced or even avoided. Thereby, the human's vision can be improved much more efficiently than in the prior art.

With respect to these features, the present invention is different from the prior art process and device described by Kasten et al. (1997; loc. cit.) which does not disclose the continuous monitoring of the residual performance of the visual system of the person to be trained. Rather, the Kasten device keeps the training area of the visual field constant, stimulating over and over again areas where vision has already been restored or in which vision was not at all impaired. Thus, the prior art device presented stimuli independent upon the persons'actual performance. In said device, after experiencing some training benefit, the restored areas are still continuously being trained, even though this is no longer required. Thus, the visual presentation paradigm disclosed in the prior art is both laborious, time-consuming and in large part unnecessary. In fact, persons to be trained have reported that the prior art training is too long and boring.

In addition, with the prior art method it is not possible to detect and specifically treat areas of "only" deteriorated vision or of residual visual functions or of partial visual system injury. Because of the time-consuming training, in the prior art process, including a training of areas or zones showing optimum results of visual performance, there has been a long-felt need to conceive of a optical stimulus presentation paradigm which is shorter in duration and more efficient in its use. In the present invention, we have therefore conceived a visual system training process and device by introducing the innovative step of continuously monitoring the performance of the person in need of a training of the visual field and stimulating only those regions of the visual system which are "only" of deteriorated vision or partially injured.

Thus, in accordance with the present invention, we developed a more efficient approach by concentrating the visual stimulus presentations to those areas of the visual field in which a more efficient rehabilitation progress can be expected.

To overcome the limitation of the prior art devices, we now propose in accordance with the invention to first locate, define and characterize the zones of impaired, i. e. deteriorated vision or residual visual function or partial visual system injury. These zones of deteriorated vision or impaired vision or partial visual system injury are hereinafter shortly referred to as transition zones (see FIG. 1). Such transition zones may, for example, be found with aged people whose vision, for example lateral vision, becomes more and more restricted. Transition zones may also be found with people whose visual system was influenced as a result of a brain injury, stroke or similar event. Another example are transition zones between zones of completely maintained and wholly lost ability to visually discriminate between colours, shapes or movements. Within said transition zones, there are located the training areas or zones which are defined in the next step of the present procedure.

In a preferred embodiment of the invention, the size and location of said training area or areas within said transition zone are selected in accordance with the size, location and kind of the zone of partial visial system deterioration, of residual visual fimction or visual deficit of said human. In other words: It has to be checked carefully, which parts of the visual system of said human have the greatest need for the subsequent training by presenting optical stimuli.

Then, based on the individual person's performance which is determined continuously or intermittently during said training, we propose to present the training stimuli in those transition zones. In preferred embodiments of the invention, optical and preferably light stimuli are presented to the person's visual system. It is even more preferred that light stimuli of different colour, luminance, intensity and/or shape are presented to the visual system of the person to be trained. Such light stimuli can be presented as static light stimuli or a series of light stimuli in a sequence generating an impression of a moving object.

This "transition-zone based stimulus presentation" is based on the consideration that there are areas of "only" deteriorated vision of a person or partial visual functions where vision is neither intact nor completely damaged but where some neuronal structures survived the injury. It is reasoned that these surviving neurons, as long as their number exceeds a certain minimum ("hypothesis of minimal residual structure"), mediate the return of vision due to training, and therefore their stimulation by training would be the critical step to be taken. As a consequence, to overcome the previously recognized problems of inefficient visual field stimulation, we therefore devised a new presentation strategy by selectively stimulating these regions ("transition zones") using a computer-controlled stimulation device.

Specific algorithms were developed to follow the above presentation strategy, which algorithms allow the highly efficient training of areas of visual system dysfunction or malfunction. The detailed steps of the training procedure are described below with respect to stimulating specific areas or zones of the human visual system by optical stimuli.

During the training step, changes in the characteristics of the visual system of the human trained are recorded. In other words: The performance of the person trained in view of visually recognizing the optical stimuli presented and himself/herself presenting the desired reaction on said visual recognition step is recorded by the system/device of the present invention. To give just one example: The reaction time of the trained person on an optical stimulus presented to the transition zone of his/her visual system is measured, and the time elapsed between the emission of the optical stimulus and the reaction given (for example by pressing a button of the device), relative to an average time value measured before for the trained person as a base line value, is taken as the performance of the person with respect to the trained area of the transition zone. However, this example is not to be considered as limiting the invention; any other appropriate step may be taken, too, in order to continuously or intermittently record changes in the characteristics of the human's visual system.

Based on the continuous recordal of the changes in the characteristics as decribed above, the location and definition of the transition zone is adapted to said changes. This may also be conducted continuously or intermittently. In other words: Depending upon the performance of the trained person in processing the presented optical stimuli by the visual system, the transition zone is newly defined. Without wanting to be bound by the explanation, it can be assumed that, due to the effective training of the defined transition zone, the vision of the trained person is improved in said transition zone, for example by improving any deteriorated fimction of the visual system (e. g. peripheral vision, visual acuity, ability to discriminate between different colours, shapes, movement; reduction of squinting; increase of the visual angle) or improving residual visual functions or removing partial visual system injuries. As a result thereof, the transition zone becomes an intact area of the person's visual system, and another part of the defective area may become (and is defined to be) a transition zone for another step or series of steps of training by presenting optical stimuli to said new transition zone of the human's visual system (see also FIG. 1).

Figure 1:
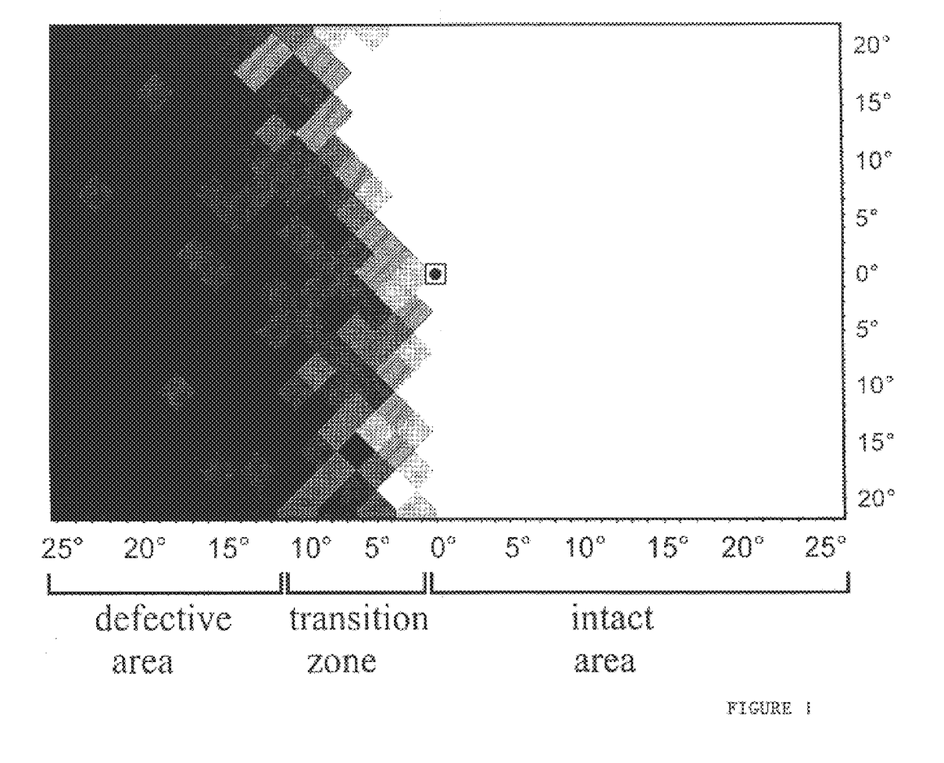
FIG. 1 shows an assumed visual field of a person suffering from partial blindness which visual field is divided into a sector or zone where the person's visual functions are not impaired ("intact area"), a sector or zone of partial visual system injury ("transition zone") and a sector or zone of substantially complete visual system injury ("defective area").

By reiterating the above-described steps, the human's intact visual field is continuously extended into zones which were previously located and defined to be transition zones, and said transition zones are continuously extended into zones which previously were zones of deteriorated vision or zones of less residual visual function or zones of substantially complete visual system injury, i. e. defective zones (see FIG. 1).

Using this computer program-based training, we conducted two independent placebo-controlled clinical trials in humans suffering from CNS damage. While our process and device can be used for any disorder of the visual system without that the present study is to be considered as a limitation to such severe disorders, the persons trained and evaluated in the present study were those with visual cortex or optic nerve injury. We were able to show for the first time, in a strictly controlled clinical trial, a significant reduction of partial blindness by training the persons'visual system through repetitive stimulation of the visual field, when stimulating areas of residual functions or "transition zones".

Training Software and Training Procedure

Training was carried out with a personal computer for use at home where persons to be trained practiced on a regular basis. The preferred embodiment of the present invention is daily training for 1 hr in a darkened room for an extended time period, as for example a 6-months period as employed in this test. However, any other training period may also prove efficacious.

As the prior art devices have been inefficient, a special algorithm was developed which produced on a monitor an emission of light stimuli effecting a repetitive visual stimulation of the transition zone located between the intact and damaged visual field sector of the human to be trained. In a first step, the "transition zone" was located, defined and characterized. i.e. there occured a determination of the exact residual visual function in said transition zone with respect to location, size and kind.

After said first step, there was defined a training area which is located within said transition zone. Said training area is a region within the transition zone where a regeneration of the neuronal structures of the person's visual system could be expected due to the results of the definition and characterization of the transition zone in the first step, e. g. due to the presence of a minimum of remaining neuronal structures.

In a subsequent step, there was conducted a stimulation of the area of impaired function based on the performance determined in the first and second steps. This approach is more efficient because it does not stimulate intact areas of the visual field but just those areas which are characterized by impaired functions.

Also, unlike prior art devices in which the program only stores the data for a later analysis, the present invention adapts, on a continuous or intermittent basis, training algorithms to the visual system performance in or near the areas of impaired functions.

In addition, daily therapy results can be stored on suitable storing media like a tape or a disc which permits monitoring of compliance and which allows the therapy strategy to be adapted to the progress of the person.

The invention is hereinafter described in detail with reference to the Figures. While the description of the invention mainly relates to a training of persons whose visual system is severely damaged, all details of the invention, i. e. the process and the apparatus, can be applied mutatis mutandis by a skilled person to the training of persons whose visual system deteriorates smoothly due to an ageing of said person and als to persons whose regular vision is to be trained in order to maintain the quality of the vision on a high level. Insofar, the description of the training procedure in connection to persons with a severely damaged visual system is not to be construed as a limitation of the invention.

In the Figures,

FIG. 2 shows a computer-based high-resolution perimetry ("HRP"), wherein FIG. 2A represents the assumed visual field of a person in the form of a circle, wherein the defective area is seen on the left side (shaded half of the circle) and the central square represents the area assessed by computer-based HRP; FIG. 2B represents an enlargement of the central square of FIG. 2A, wherein the right white area is the zone of intact visual function, the grey area is the area of inconsistent responses on optical stimuli (lighter grey indicates a greater number of "hits"), and the black area represents a zone of defective visual function; FIG. 2C shows the enlarged left part of FIG. 2B, showing islands of residual visual functions; FIG. 2D shows the same area as FIG. 2C, but after restitution training; and FIG. 2E shows the difference between FIG. 2D and FIG. 2C in order to show an increase or decrease of visual performance. Is is noted that the presentation of the visual stimuli is based on the shape and location of the "grey" zones, i.e. the transition zone where variable performance is noted. The majority of the visual stimuli are presented in this transition zone and not in the intact visual field sector. In contrast to prior art devices, in which stimuli are presented either at random in the entire visual field or in which a stimulus is moved line by line, in the present invention that stimuli are presented only in the "transition zone".

The invention is explained in further detail with reference to the Figures and the preferred embodiments without being restricted to these preferred embodiments.

The computer algorithms for the step of presenting visual stimuli to the human's visual system are such that the monitor presents a fixation point, which can be presented in any part of the monitor. The fixation point serves to a fixation of the person's view to a certain point in order to allow an adjustment of the person's angle of view. In succession, additional visual stimuli are presented in or immediately adjacent to the transition zone, the location of which is determined in the previous step and changed in accordance with the person's performance. In the prior art device published by Kasten et al., the visual stimuli were presented independent of the persons'actual progress and were therefore inefficient and laborious. In contrast thereto, the visual stimuli are presented in the present invention perdominantly in or adjacent to the transition zone, i. e. an area with only a partial visual system injury or deteriorated vision.

As in the prior art, in the present invention the person responds to each optical stimulus to the transition zone of the visual system by pressing an appropriate key on the keyboard of the computer. In contrast to the prior art device disclosed by Kasten et al. (1997), however, there is now employed an individually adapted training procedure to increase the probability of therapeutic benefit and training compliance by avoiding non-challenging training levels, while, at the same time, being able to reduce the total number of visual stimuli to achieve the same effect.

It should be apparent from this disclosure that it is beneficial to limit the area of training to those parts in the visual field which are only partially injured or deteriorated. Of course, the actual stimulus presented can vary in size, luminance, shape or color and it can be presented by various means, such as a projection screen, a simple computer monitor or other visual projection devices such as virtual reality gargles or helmet. The type of stimulus as well as the way by which it is presented is not limited, as long as it is acertained that the location of the stimulus presentation is adapted to the persons individual deficit and as long as the majority of the stimulus presentations are given in "transition zones", i.e. areas of impaired visual functions.

The theory behind this visual field stimulation algorithm assumes that repetitive neuronal activitation restores functions which are otherwise lost, compromised or disused. The advantage of the present invention over prior art devices is that by focusing the person's attention onto the area of the visual field impairment, neuronal activation is larger compared to the prior art situation where the person has to attend to a small light stimulus which moves along a line from the deficient to the intact area of the person's visual field. From this argument it should be apparent that focusing attention to the partially injured sectors of the visual field would result in a relative increase of neuronal activity by instructing the persons to focus their attention on exactly those areas which are injured but where residual visual functions can still be detected. It would not be of benefit to also present a great number of stimuli in the intact visual field sectors.

The above argument does not mean to imply that functions in the blind or substantially completely defective field can never be regained, i.e. in that zones in which previously no visual stimuli could be responded on. Rather, as our clinical trial has shown, even in those areas completely devoid of visual functions training may restore visual function. FIGS. 2C to 2E show an example. Note that areas which were previously blind (black squares in FIG. 2C) are reversed to see again after some months of training (white squares in FIG. 2D).

The timing of the training also does not predict how fast visual field deficits are restored. Whereas some persons need weeks or months for functions to return, in others the improvement is rapid. Therefore, the present invention does also not imply that training requires a particular time period.

Another advantage of the present invention is that areas which emerge as deficient due to the training can be specifically trained. Note in FIGS. 2C to 2E areas where performance declined due to training. The prior art devices never considered this possibility that functions can also decline in response to the training. Consequently, also with respect to this fact an adaptive procedure is of benefit. Again, stimulus presentation would be focused on those areas of the visual field which show deficits.

This raises the problem of how to define the area of the visual deficit. There are many ways whereby the partially injured brain area can be defined. In theory, any lack of response to visual stimuli, an extended reaction time to the stimuli or problems in identifying the stimuli would qualify to define areas of visual deficits. As described in the prior art, visual deficits can be documented (a) by altered thresholds during testing of the visual contrast sensitivity function; (b) by a reduced reaction time; or (c) by the absence of a reaction to the stimulus by the person, with or without conscienceness. Again, the present invention does not make any assumption as to how the deficit of the visual function is defined, as long as the majority of the training stimuli are presented in the area of the visual field which corresponds to the partially impaired function ("transition zone").

Testing the Efficiency of the Program in Clinical Trials

The following trial—and the characteristics of the persons—is chosen to document that the current invention is able in principle to reduce visual field defects. The examples chosen are in no way meant to imply that visual training is only effective in these and not in any other persons or in persons with different visual field impairment. While the preferred embodiment is aimed at persons with lesions of the nervous system, the present invention may also be useful by anyone skilled in the art to treat other disorders of the eye or visual system that do not affect the nervous system.

In order to provide a documentation of the effectiveness of the current invention, we conducted two clinical trials. The persons participating in the trials were selected from a larger pool of 130 persons with either optic nerve injury or damage to the primary visual cortex, They were screened on the basis of predetermined inclusion and exclusion criteria, and baseline assessment was carried out. The choice of the inclusion and exclusion criteria was solely selected for the purpose of reducing performance variance within the groups of persons. They were not selected to imply that person not fillfilling these criteria can not be treated. In fact, the current invention is useful for any disorder of the visual system.

The data reported here are from two independent clinical trials with an experimental and a control group each: In the first trial two groups, experimental and control, of optic nerve injury persons were matched according to age of the person (blind conditions, n=19); in the second trial persons with post-chiasmatic injury were randomly assigned (double-blind, n=19). Thereafter, the persons were instructed to train with visual tasks on the monitor at home.

The detailed description which now follows is only one preferred embodiement of the current invention. It is not meant to be limiting, neither with respect to the kind of stimulus which is presented, nor the amount of training required nor the type of the visual system disease. It is solely meant as an illustrative example.

Figure 2:
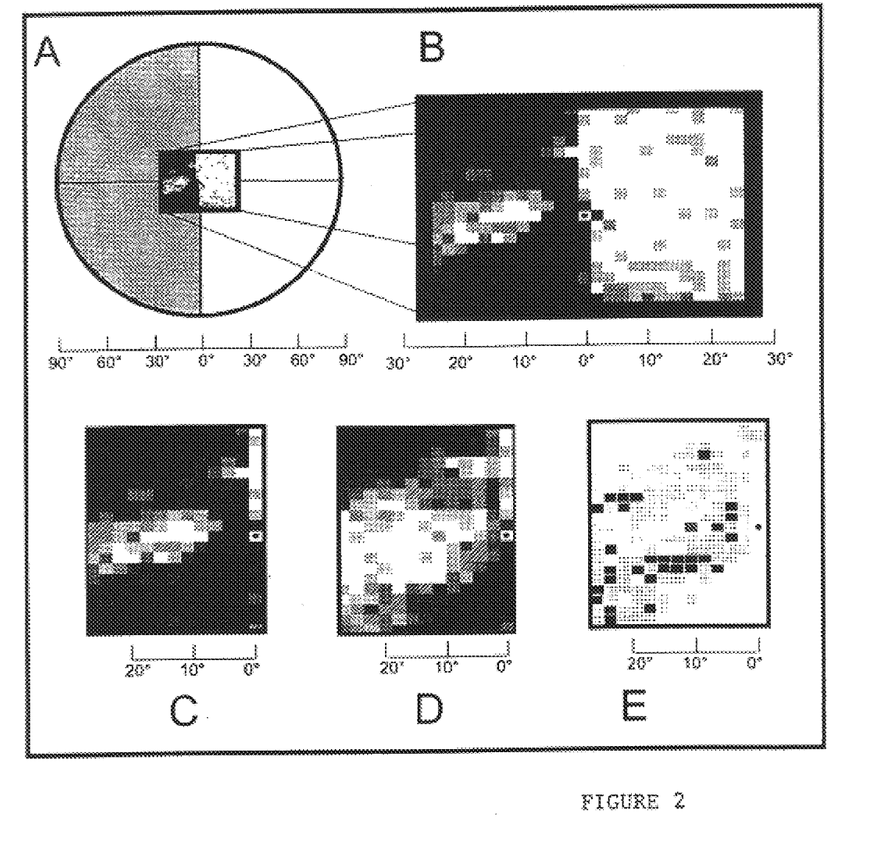

In HRP, 500 stimuli with luminance clearly above detection threshold were presented on a 17" computer monitor (see FIG. 2) . The person was required to constantly fixate on a fixation point (center star) and press a key within 750 ms. To ensure proper fixation during home training, the fixation point (a star of 4 mm diameter) randomly changed its color from bright-green (95 $cd/m^2$) to bright-yellow (100 $cd/m^2$), whereupon the person was required to press any key within 500 ms.

White, bright stimuli were presented in succession for 150 ms duration, each at 500 different positions (25×20 grid; dark monitor screen; stimulus size (SS) 0.15°; stimulus luminance (SL) 95 cd/m$^2$; background luminance (BL) <1 cd/m$^2$). Perimetry tasks and training were performed with a chin support to assure a stable head position and a fixed 30 cm distance from the monitor. The overall resolution of HRP was about four times greater than that of TAP (E. Kasten, S. Wuest & B. A. Sabel, J. Clin. Exp. Neurophysiol., in press).

TAP is a static perimeter used in routine clinical practice where the visual field up to 30° eccentricity is determined using 191 stimuli with near threshold luminance (R. Fendrich, C. M. Wessinger, M. S. Gazzaniga, Residual vision in a scotoma: Implications for blindsight, Science 258, 1489–1491 (1992)). Proper fixation of the eye was monitored using a video camera. TAP has methodological limitations, however, because (a) the persons subjective criteria may change over time when responding to stimuli near threshold; and (b) the resolution is relatively low. Therefore, TAP performance was chos en as a secondary outcome measure. The analysis of all perimetry procedures included only values obtained in the area in which training took place (treatment group) or an equivalent area in the placebo group. Visual acuity was measured with Landoldt ring values from which the minimal angle of resolution was calculated. In addition, standardized catamnestic interviews were conducted to determine whether treatment led to subjective improvements of vision in everyday life.

Final Outcome Measures and Statistics

After 150 h (about 6 months) of training, final outcome evaluation was carried out using the same procedures for baseline assessment. For statistical analysis of parametric data, a two-way ANOVA with subsequent post-hoc comparisons was calculated for each study. Student's t-test was used f or individual al group comparisons.

Person Selection

The trial was approved by the local medical ethics committee. Persons included in the study had to have both a visual field defect and post-chiasmatic or optic nerve damage as shown by CT, MRI, surgical records or ophthalmoscopic documentation of optic nerve atrophy. Persons were not entered if any one of the following exclusion criteria applied (no. of excluded cases are given in brackets):

- Insufficient fixation ability (n=11);
- neglect (n=1);
- non-optic nerve heteronymous visual field defect (n=7);
- disorders of the eye (n=9);
- no residual vision (n=2);
- no visual deficit (n=1);
- age >75 yrs (n=4);
- age <18 yrs (n=1);
- died (n=2);
- lesion age <12 months (n=3);
- epilepsy or photosensitivity (n=2);
- cognitive deficits (n=12);
- not willing to participate in trial (n=27); and
- no shows after initial screening (n=10).

From a total number of 130 persons screened, only 38 were entered into the trial.

Baseline Assessment

There were no differences in the base-line characteristics between the groups with respect to age, sex, classification of the injury or injury size (see Table 1). After the initial screening, we obtained informed consent, and persons attended one practice session to familiarize themselves with the diagnostic program, "PeriMa", (E. Kasten, H. Strasburger, B. A. Sabel, Programs for diagnosis and therapy of visual deficits in vision rehabilitation, Spatial Vis. 10, 499–503 (1997); see FIG. 2) and the monocular Tübinger automatic perimeter 2000 (TAP) under standardized environmental luminance conditions.

This was followed by 2 to 4 separate sessions of baseline evaluation with HRP. The accumulated values of these repeated measures served as the baseline value. Thereafter, the persons were assigned either to the treatment or placebo group.

The results are shown in the subsequent Table 2 in mean ±SE. The data were analyzed by a two-way ANOVA with post-hoc planned comparisons using the LSD test. F-values were taken from the two-way ANOVA with type of training as independent factor A and time (before and after the training) as dependent factor B. Significant differences are shown as comparison to baseline # or between groups at the respective time points (§).

*$p<0.05$; $p<0.025$; *$p<0.01$.

(*) trend of $p<0.10$. It has to be noted that both groups differed significantly in the number of hits in TAP at both time points (+$p<0.01$).

$ These values only include the performance from the damaged half of the visual field. ° degrees of visual angle from zero vertical meridian.

The change over baseline data were analyzed were analyzed by students t-test.

TABLE 1

Base-line characteristics of the study participants according to treatment

| Characteristics | restitution group (n = 19) | placebo group (n = 19) |
|---|---|---|
| Age of patient (yrs) | 47.7 ± 12.9 | 55.3 ± 16.2 |
| Sex: | | |
| male | 11 | 13 |
| female | 8 | 6 |
| Classification of injury | | |
| age of lesion | 6.8 ± 11.4 | 7.2 ± 6.3 |
| post-chiasmatic injury | 9 | 10 |
| due to trauma | 4 | 0 |
| due to stroke | 2 | 8 |
| due to other | 3 | 2 |
| optic nerve atrophy | 10 | 9 |
| due to trauma | 4 | 3 |
| due to neuropathy | 3 | 3 |
| due to other | 3 | 3 |
| size of visual field defect in percent* | | |
| ≦25 | 4 | 4 |
| ≦50 | 9 | 8 |
| ≦75 | 3 | 4 |
| >75 | 3 | 3 |

TABLE 2

Diagnostic values of visual functions before and after training according to treatment groups

| | Baseline | | Final outcome | | change over baseline at final outcome | | |
|---|---|---|---|---|---|---|---|
| Characteristics | restitution | placebo | restitution# | placebo | restitution | placebo | F- value |
| Post-chlasmatic injury | | | | | | | |
| no. hits in HRP | 97.3 ± 19.2 | 92.3 ± 12.0 | 116.9 ± 19.8* | 83.4 ± 11.7§*** | 19.6 ± 6.2 | −7.8 ± 8.5** | 6.77** |
| border position in ° | 5.4 ± 1.5 | 5.1 ± 2.3 | 10.3 ± 1.8*** | 4.2 ± 1.8§*** | 4.9 ± 1.7 | −0.9 ± 0.8** | 9.68*** |
| no. of misses in TAP | 53.0 ± 9.1+ | 69.2 ± 11.2 | 50.1 ± 9.2+ | 71.9 ± 12.0 | −2.9 ± 3.0 | 2.7 ± 3.0 | 1.89 |
| TAP border position in ° | 3.51 ± 1.0 | 3.43 ± 0.99 | 3.94 ± 1.0 | 2.92 ± 0.7§*** | 0.43 ± 0.3 | −.51 ± .34* | 3.86(*) |
| optic nerve injury | | | | | | | |
| no. hits in HRP | 203.2 ± 27.8 | 197.7 ± 37.0 | 312.8 ± 24.4*** | 227.8 ± 45.7 | 109.6 ± 15.5 | 30.1 ± 12.7*** | 15.31*** |
| border position in ° | 8.5 ± 1.8 | 5.8 ± 1.0 | 14.4 ± 2.4*** | 10.1 ± 1.5(*) | 5.8 ± 1.2 | 4.3 ± 0.7 | 0.43 |
| no. of misses in TAP | 87.9 ± 13.9 | 94.6 ± 17.6 | 63.9 ± 10.6*** | 89.8 ± 15.8 | −24.1 ± 3.8 | −4.8 ± 3.85*** | 3.76(*) |
| TAP border position in ° | 3.6 ± 0.9 | 3.8 ± 1.2 | 5.7 ± 1.0*** | 5.1 ± 1.7#** | 2.1 ± 0.5 | 1.4 ± 0.5 | 0.91 |
| acuity | 21.0 ± 5.6 | 11.8 ± 3.0 | 12.6 ± 2.3*** | 11.9 ± 3.1 | −8.4 ± 4..4 | 0.1 ± 1.52* | 5.51* |

Visual Field Enlargements

Figure 3:
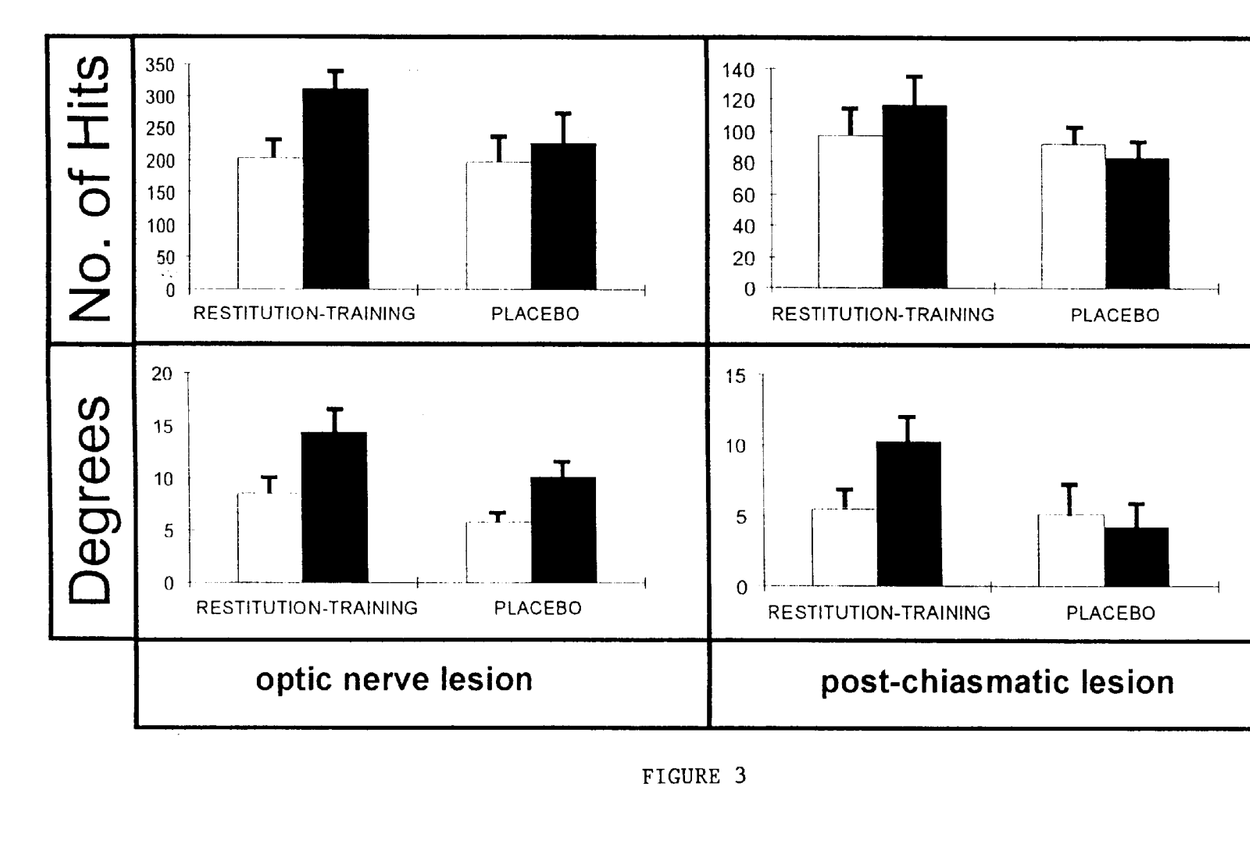
FIG. 3 shows visual functions before (white bars) and after (black bars) restitution training or placebo (fixation training) of persons which sustained either optic nerve or post-chiasmatic damage (mean ±SE). HRP data are displayed as number of detected stimuli, i.e. hits, (upper panel). The lower panel shows the position of visual field border from zero vertical meridian in degrees of visual angle.

Primary outcome measure: Both restitution groups, but not the control groups, showed significant improvements in their ability to perceive small visual stimuli well above detection threshold (HRP test) after the training (Table 2). In the visual field sector which was trained persons receiving restitution training responded to stimuli more frequently (hits) than the control group (post-chiasma persons: 29.4% over baseline, optic nerve persons: 73.6%, p<0.05). In addition, control persons showed either no improvement (post-chiasma persons: 7.7%) or significantly smaller improvements (optic nerve persons: 14.4% Table 1). Optic nerve persons thus profited most from the training (FIGS. 2 and 3).

Figure 4:
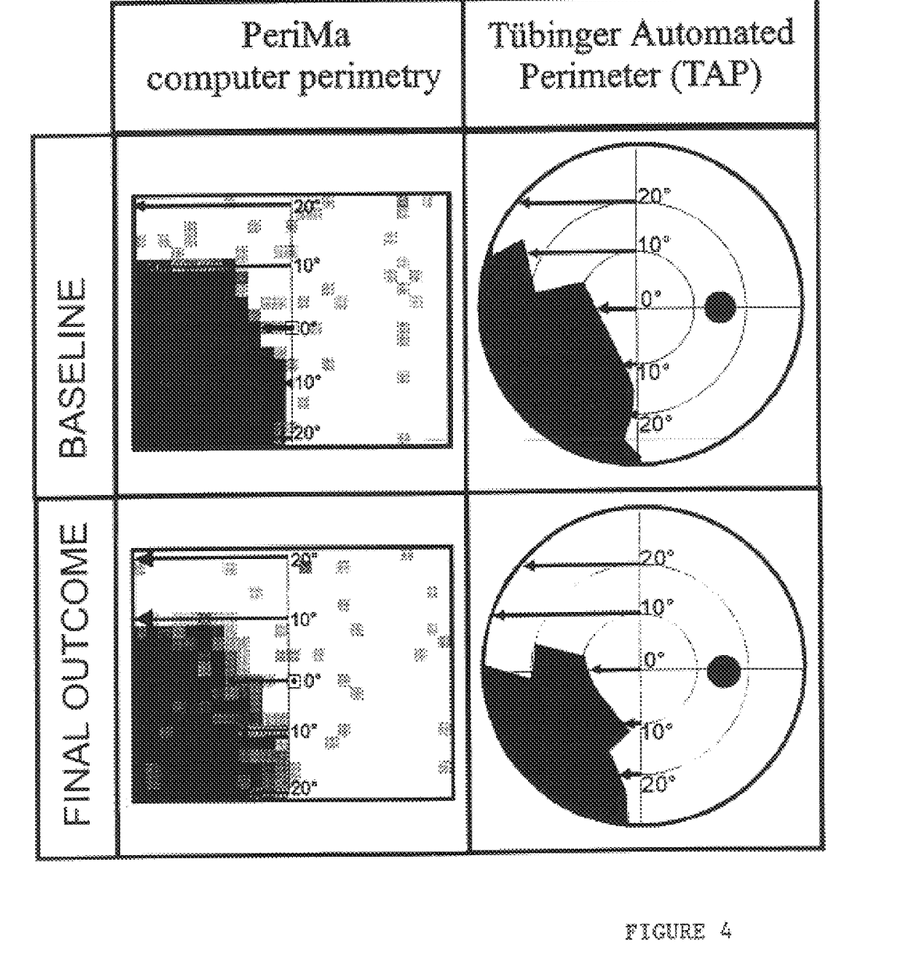
FIG. 4 shows data, wherein the border in HRP or TAP was determined by measuring the distance of the black squares (i.e. location without hits, see legend to FIG. 1) from the zero vertical meridian at the vertical position of +20°, +10°, 0°, −10° and −20° of visual a extent of visual field enlargement was determined by averaging these measurements and calculating the pre-post difference. Note that the border in HRP differs from that obtained with TAP-perimetry.

The position of the visual field border was assessed before and after treatment as well (FIG. 4). Since in some optic nerve persons the lesion was located on both sides of the visual field, here the border was determined on both sides of the zero vertical meridian. A border shift was noted in both optic nerve (5.8°±1.2) and post-chiasmatic persons (4.9°±1.7), with smaller changes (optic nerve: 4.3°±0.69, n.s.) or no changes (post-chiasma: −0.90°±0.8) in the placebo-groups. Most persons (18 out of 19) benefited from the restitution training as documented by the primary outcome measure: For HRP, the percent improvement above baseline was either smaller than 20 % (n=5), up to 50% (n=5), up to 100% (n=4), or in 4 persons, above 100% (maximum in one person: 200%).

Secondary outcome measures: In optic nerve persons the area of absolute defect as measured by TAP decreased significantly in the restitution group but not in the control group. In post-chiasmatic persons there was no such difference in TAP performance. Calculating the visual field size by determining the visual field border using TAP data in degrees of visual angle, restitution training led to a border shift, i.e. visual field size increase, of only 0.43°±0.34in the restitution and−0.5°°±0.34 decrease in the placebo group of the post-chiasmatic persons. In optic nerve persons the border shift was 2.1°±0.5 and 1.4°±0.5, respectively.

Of the 38 persons participating in the trial 30 responded to a post-trial questionnaire with which subjective improvements were checked. 72.2% of the persons receiving restitution training (n=18) but only 16.6% of the control group (n=12) reported subjective improvements of vision (chi-square=8.89, p<0.003). No noteworthy differences between the groups were noticed due to age or sex of the persons, the size or side (right/left) of the visual field defect and the age of the injury.

Functional Significance of Computer-Controlled Training

We have shown for the first time that visual restitution training on a computer monitor leads to significant visual field enlargement both after optic nerve and visual cortex injury. Fixation training (placebo) did not increase the size of the visual field in post-chiasmatic persons, although a small improvement was noticeable in optic nerve persons. About 95% of all the restitution group subjects experienced a visual field enlargement with a mean increase in light detection of 56.4% ±12.3 above baseline and an average increase of 4.9° or 5.80° of visual angle in post-chiasmatic or optic nerve persons, respectively. This magnitude of change is functionally meaningful:

Firstly, a 5° increase in visual field corresponds roughly to one half of this journal page at arms length distance, and as little as 2–3° of foveal vision are generally sufficient for reading (E. Aufhom, Soziale Integration in Abhängigkeit von der Prognose, in: W. Hammerstein, W. Lisch (eds.), Ophthalmologische Genetik, Stuttgart (1985), pages 368 to 373).

Secondly, the large majority (about 72.2%) of our persons receiving restitution training reported subjective improvements.

The neurobiological mechanisms involved in visual restitution are currently unknown, but converging findings in animals and humans provide some initial clues. We propose that training reactivates surviving neuronal elements of the partially damaged structure itself, i.e. the border region ("transition zone") or islands of residual vision which exist in some persons with visual cortex injury (R. Fendrich, C. M. Wessinger, M. S. Gazzaniga, Residual vision in a scotoma: Implications for blindsight, Science 258, 1489–1491 (1992)). Transition zones, usually located between the intact and damaged area of the visual field (see grey areas in FIGS. 2 and 4) are proposed to be a functional representation of surviving neurons in partially injured tissue (B. A. Sabel et al (1997), loc. cit.; E. Kasten et al. (in press), loc. cit.). According to the "minimum residual structure" hypothesis (B. A. Sabel (1997), loc. cit.), survival of as little as 10–15% of neurons is sufficient for recovery of vision to occur, i.e., very few residual neurons in these areas may be sufficient to reactivate visual functions (J. Sautter et al. (1993), loc. cit.). This may also explain why persons with optic nerve injury profited more from restitution training in our trial because their transition zones are particularly large (i.e., areas of diffuse injury, data not shown). We therefore propose that residual neurons in the partially damaged visual system which activate visual targets only insufficiently, perhaps because of "disuse", become activated by repetitive visual stimulation during restitution training.

It is conceivable that receptive field enlargements occur which are similar to those shown by Kaas (J. H. Kaas et al. (1990), loc. cit.). He found spontaneous cortical map enlargements of 5° over the course of several months in monkeys after retinal lesions, a value which is almost identical to the 4.9°–5.8° visual field enlargement seen in our persons. Since regular visual stimulation of the damaged border region by restitution training can significantly enlarge the visual field, the plasticity potential of the adult visual system can be utilised for therapeutic purposes in man. The use of an in-home computerized training program is both cost-effective and convenient with no apparent side effects.

In conclusion, our study extends the results of previous animal studies to humans and illustrates that persons who suffer from partial blindness benefit from restitution training, regaining some of their lost vision. The general implications of our findings is that computer-based training programs can significantly increase human brain fimction.

What is claimed is:

1. A process for training the visual system of a human by presenting optical stimuli to said human, said stimuli being presented to a zone within the intact visual field of said human and to a zone outside the intact visual field of said human, the latter zone comprising a zone to be trained, thereby allowing an improvement of the vision in said latter zone, said process comprising the steps of locating and defining a zone of deteriorated vision or residual visual function or partial visual system injury ("transition zone") within the human's visual system;

defining a training area which is located within said transition zone;

training the human's visual system by presenting visual stimuli to the human's visual system, the majority of said visual stimuli being presented in or near said transition zone;

recording changes in the characteristics of the human's visual system;

adapting the location and definition of the stimulus presentation to said transition zone according to said changes; and reiterating the previous steps continuously so as to extend the human's intact visual field into said transition zone and said transition zone into a zone of more deteriorated vision or a zone of less residual visual function or a zone of substantially complete visual system injury.

2. The process of claim 1, wherein the size, location and kind of said training area are selected in accordance with the size, location and kind of the zone of partial visual system deterioration, of residual visual function and/or visual deficit of said human.

3. The process of claim 1, wherein light stimuli are presented to the person's visual system as the visual stimuli, preferably light stimuli of different colour, luminance, intensity and/or shape.

4. The process of claim 1, wherein the step of presenting light stimuli to the person's visual system comprises presenting a fixation point to the person's visual field allowing a control of the person's angle of view.

5. The process of claim 1, wherein substantially all light stimuli are presented to the person's visual system in or immediately adjacent to the transition zone.

6. The process of the claim 1, wherein the step of presenting light stimuli to the person's visual system is conducted on a computer screen, on a video screen, on a projection screen or by visual projection devices like virtual reality gargles or helmets.

7. The process of claim 1, wherein the recordal of changes in the characteristics of the person's visual system comprises a recordal of the responsiveness, of the colour recognition, of the shape recognition and/or of the localization of the visual stimuli by the person.

8. The process of claim 1, wherein the steps of locating and defining said transition zone, defining said training area, presenting visual stimuli, recording changes in the person's performance, adapting the location and definition of the transition zone and reiterating the previous steps are controlled by a central data processing means.

9. A device for training the visual system or vision of a human by presenting optical stimuli to said human, being presented to a zone within the intact visual field of said human and to a zone outside the intact visual field of said human, the latter zone comprising a zone to be trained, thereby allowing an improvement of the vision in said latter zone, said device comprising a central data processing means for recording, storing, processing and emitting data from the other means of the device;

at least one optical stimuli presenting means;

a fixation point means allowing the fixation of the person's view;

means for entering the person's response on optical stimuli perceived;

means for allowing a control of said at least one optical stimuli presenting means in accordance with the performance of the person responding on optical stimuli perceived.

10. The device of claim 9, said device enabling the steps of locating and defining a zone of deteriorated vision or residual visual function or partial visual system injury ("transition zone") within the human's visual system;

defining a training area which is located within said transition zone;

training the human's visual system by presenting visual stimuli to the human's visual system, the majority of said visual stimuli being presented in or near said transition zone;

recording changes in the characteristics of the human's visual system;

adapting the location and definition of the stimulus presentation to said transition zone according to said changes; and reiterating the previous steps continuously so as to extend the human's intact visual field into said transition zone and said transition zone into a zone of more deteriorated vision or a zone of less residual visual function or a zone of substantially complete visual system injury.

11. The device of claim 9, additionally comprising means for fixing and/or supporting the head of the person.

12. The device of claim 9, wherein said visual stimuli-emitting means are light emitting means, preferably light emitting means for light of variable colour, luminance, intensity and/or shape.

13. The device of claim 9, wherein said light emitting means is a computer screen, a video screen, a projection screen or a visual projection device like virtual reality gargles or helmets.

14. The device of claim 9, wherein said fixation point means allowing the fixation of the person's view is a coloured mark, preferably enabled to change the colour in order to allow a control of the person's angle of view.

15. The device of claim 9, wherein said control means allows a control of said at least one optical stimuli presenting means in accordance with the quality of the response on said optical stimuli.

16. The use of the device of claim 9 for training the vision of persons operating technical machines, weapon systems or land vehicles, water vehicles and air vehicles.

17. The use of the device of claim 9 for training the vision of aged persons.

18. The use of the device of claim 9 for training the vision of shortsighted or farsighted persons.

19. The use of the device of claim 9 for training the vision of children, preferably squinting children.

20. The use of the device of claim 9 for training the vision of persons having experienced a partial visual system injury.

21. The use of the device of claim 9 to for training the vision of normal-sighted persons for maintaining the vision.

* * * * *

UNITED STATES PATENT AND TRADEMARK OFFICE
CERTIFICATE OF CORRECTION

PATENT NO. : 6,464,356 B1 Page 1 of 1
APPLICATION NO. : 09/784450
DATED : October 15, 2002
INVENTOR(S) : Sabel et al.

It is certified that error appears in the above-identified patent and that said Letters Patent is hereby corrected as shown below:

In Col. 9, line 29
replace "gargles"
with --goggles.--

In Col. 16, line 3
replace "gargles"
with --goggles.--

In Col. 16, line 65
replace "gargles"
with --goggles.--

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

PATENT NO.        : 6,464,356 B1                                           Page 1 of 1
APPLICATION NO. : 09/784450
DATED             : October 15, 2002
INVENTOR(S)       : Sabel et al.

It is certified that error appears in the above-identified patent and that said Letters Patent is hereby corrected as shown below:

In Col. 9, line 29
replace "gargles"
with --goggles.--

In Col. 16, line 3
replace "gargles"
with --goggles.--

In Col. 16, line 65
replace "gargles"
with --goggles.--

Signed and Sealed this

Twenty-first Day of August, 2007

JON W. DUDAS
*Director of the United States Patent and Trademark Office*